United States Patent [19]

Takahara et al.

[11] Patent Number: 5,665,964

[45] Date of Patent: Sep. 9, 1997

[54] PARTICLE COMPONENT ANALYZING APPARATUS, AND EQUIVALENT PARTICLE DIAMETER MEASURING METHOD USING SAME

[75] Inventors: Hisao Takahara; Yukihiko Takamatsu; Yasuhiro Tanibata, all of Tokyo, Japan

[73] Assignee: Yokogawa Electric Corporation, Tokyo, Japan

[21] Appl. No.: 775,449

[22] Filed: Dec. 30, 1996

Related U.S. Application Data

[60] Continuation of Ser. No. 559,456, Nov. 15, 1995, abandoned, which is a division of Ser. No. 329,895, Oct. 27, 1994, Pat. No. 5,510,611.

[30] Foreign Application Priority Data

Feb. 25, 1994 [JP] Japan .................... 94/27740
May 11, 1994 [JP] Japan .................... 94/97309

[51] Int. Cl.$^6$ .................................................. G01J 3/50
[52] U.S. Cl. .................... 250/226; 250/372; 250/339.01; 324/636
[58] Field of Search .......................... 250/226, 573, 250/574, 576, 221, 222.1, 222.2, 372, 373, 339.01, 339.05, 339.07, 339.14; 356/311, 316, 326, 328, 335; 324/633, 635, 636, 637, 638, 639, 644, 615; 73/23.37, 28.01

[56] References Cited

U.S. PATENT DOCUMENTS 3,944,797  3/1976  Coulter et al. .................... 364/555
4,369,404  1/1983  Flygare et al. .................... 324/636
5,124,653  6/1992  Andresen et al. .................... 324/636
5,510,611  4/1996  Takahara et al. .................... 250/226

Primary Examiner—Edward P. Westin
Assistant Examiner—John R. Lee
Attorney, Agent, or Firm—Moonray Kojima

[57] ABSTRACT

A particle component analyzing apparatus and method using a microwave induced plasma to perform element analysis of particles, such as particles existing in a clean room; wherein an aspirator scans a filter to draw particles collected on the filter, and using the microwaves to excite the drawn particles to cause generation of an emission spectrum having a plurality of wavelengths indicative of the elements of the particle, which are measured by a plurality of monochrometers, and converted by an optoelectric converter into electrical signals to identify the different elements in the particle. The invention uses means for obtaining the cube roots of the outputs from the optoelectric converter. By obtaining the ratio of cube root outputs corresponding to the diameters of particles preprocessed into spherical shape of a reference element and of an element to be measured, and then by obtaining the cube root of an output from an element in a measurement sample and by multiplying it by the ratio of cube roots with respect to the reference element, there is obtained an equivalent particle diameter corrected for differences in sensitivity between the elements. Means are provided for determining the composition of a particle from the emission spectrum and for calculating the composition ratios of a plurality of elements from the different emission intensities.

10 Claims, 18 Drawing Sheets

Output of 4 Monochrometers

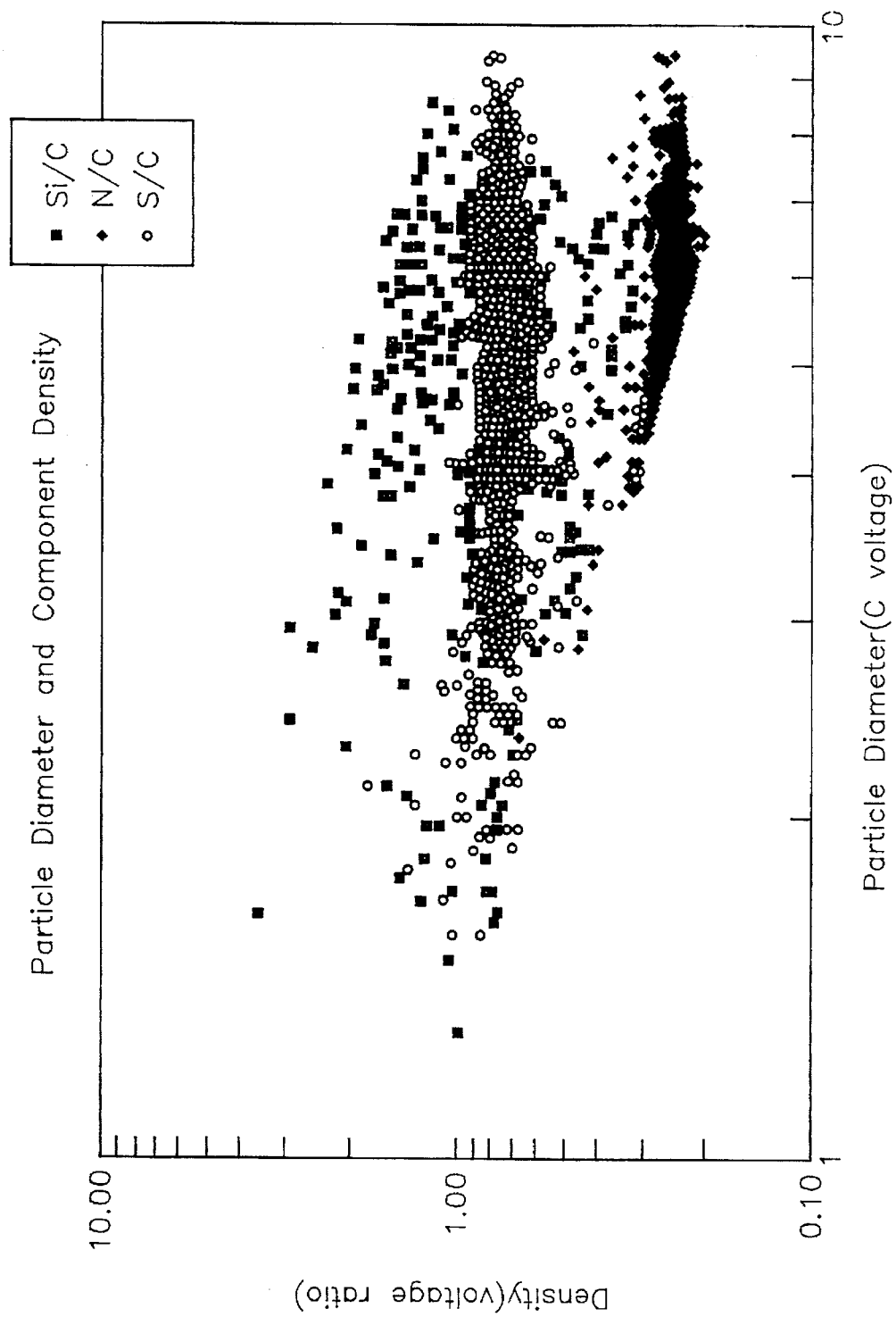

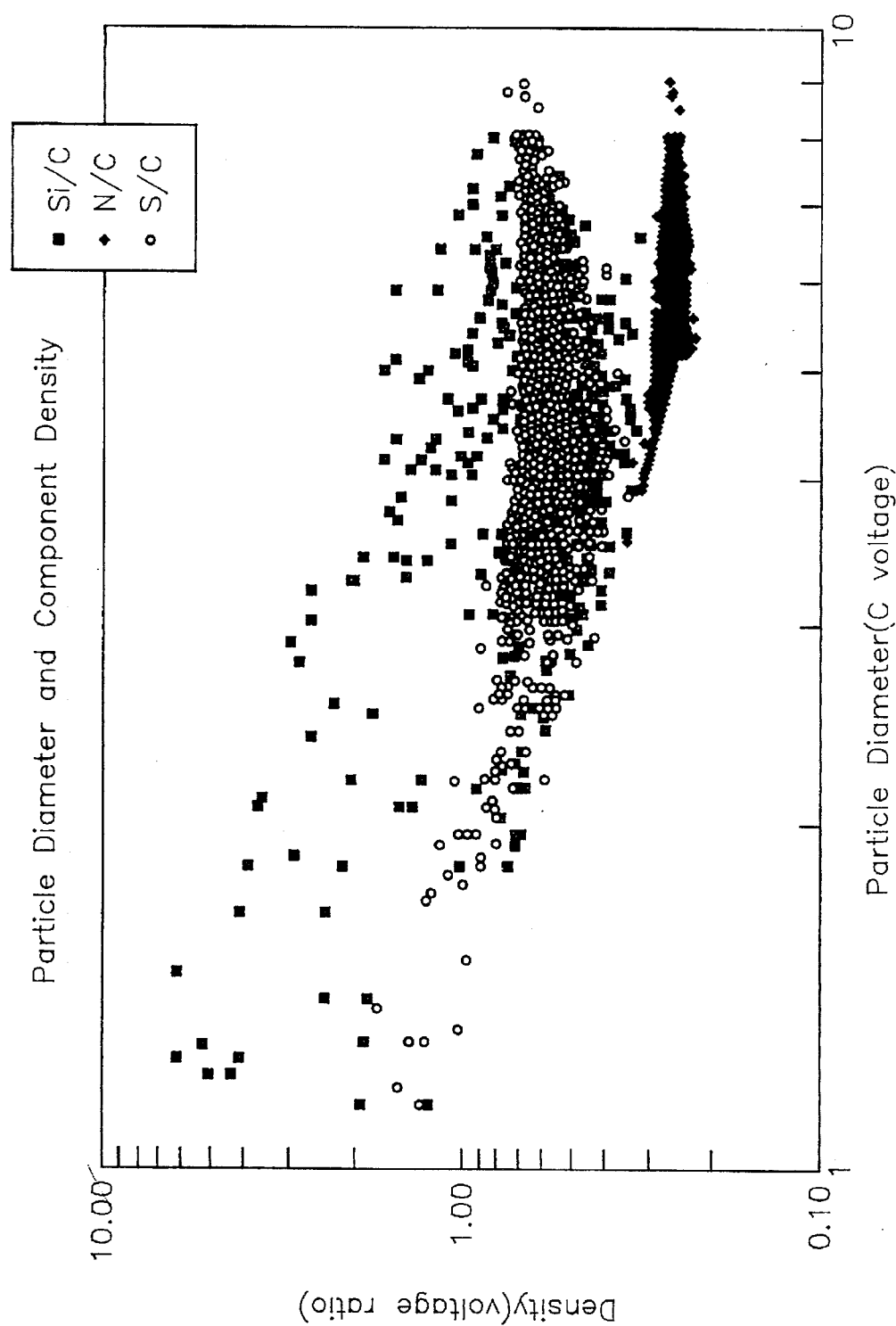

PARTICLE COMPONENT ANALYZING APPARATUS, AND EQUIVALENT PARTICLE DIAMETER MEASURING METHOD USING SAME

RELATED APPLICATIONS

This is a "File Wrapper Continuation" of Ser. No. 08/559,456 filed Nov. 15, 1995, abandoned concurrently with the filing hereof, which was a division of Ser. No. 08/329,895 filed Oct. 27, 1994, now U.S. Pat. No. 5,510,611 issued Apr. 23, 1996.

BACKGROUND OF THE INVENTION

1. Field of Invention

This invention relates to a particle component analyzing apparatus which uses a microwave induced plasma to perform element analysis of, for example, particles which float in a clean room, and to a particle composition determining method for obtaining accurate equivalent particle diameters from information obtained using such apparatus and for determining the composition of the particles.

2. Description of the Prior Art

FIG. 1 shows a conventional particle component analyzing apparatus using a microwave induced plasma. The apparatus comprises a disperser 1 having therein a filter 2, with solid particles to be measured (not shown in the drawing) adhereto thereto, and an aspirator 3 which draws up solid particles adhered to the filter 2, and feeds the particles through valve 7c into one end of a discharge tube 4. Air is removed from inside disperser 1 by a suction pump 5 and the He gas is introduced through an inlet 8 and valve 7b to maintain a pressure slightly higher than atmospheric pressure. A carrier gas (e.g. He) is applied through inlet 9 and valve 7a.

A microwave source 13 introduces microwaves into a cavity 17. A detection window 16 is disposed at the other end of discharge tube 4. An optical window 17 is disposed facing detection window 16. A focusing unit 18 is provided comprising a concave mirror 18a and a reflector 18b. The emission spectrum caused by the microwave impinging on the particles adhered to the filter causes the elements of the particles to emit an emission spectrum having a plurality of wavelengths. The emission spectrum is guided through slit 19 after being reflected by reflector 18b and then is guided into a signal processing section 20. Signal processing section 20 comprises four monochrometers 20b, each of which receives emission spectrum through one of four optical fibers 20c. The outputs of the monochrometers 20b are applied to central processing unit (CPU) 20a.

In the FIG. 1 apparatus, microwaves having a frequency of 2.45 GHz are generated by source 13 and are applied to cavity 14, and a plasma of approximately 4000°K. is created in discharge tube 4.

Solid particles guided into discharge tube 4 from dispenser 1 are atomized, ionized and excited in the plasma, and emitted as an emission spectrum as they are reduced to their base states. This emission spectrum is led out of discharge tube 4 in the axial direction thereof, then guided through optical window 17 into focusing unit 18, wherein the emission spectrum is focused, and then passed through slit 19, then separated into different wavelengths by monochrometers 20b, and then signal processed by CPU 20a. In this manner, the elements contained in the specimen particles are measured and displayed. Monochrometers 20b are provided with optoelectrical converters 20d, which output electrical signals corresponding to the strength of light of the selected wavelengths. Amplifiers 21, which are ordinary amplifiers, when FIG. 1 is considered to show a prior art apparatus, amplify the output signals from optoelectric converters 20d. The amplifiers 21 are disposed after the converters 20d. The sizes of the particles are classified according to the strength of the output signals from the amplifiers 21, such as, for example, three classes of large, medium and small.

It should be mentioned hereat that FIG. 1 shows amplifier 21 as being an ordinary amplifier when the apparatus is a conventional apparatus. When FIG. 1 is illustrative of the invention, the amplifier 21 is a cube root amplifier. The drawing distinctly shows that for the conventional apparatus, an ordinary amplifier is used as amplifier 21, and that for the illustrative embodiment of the invention, a cube root amplifier is used as amplifier 21, and FIG. 1 is to be understood be signify such dual meaning.

Returning to FIG. 1, filter 2 has a predetermined surface area, and aspirator 3 scans the filter a plurality of times, for example, 15 times, as shown in FIG. 2, and draws up the same quantity of particles each time. It is assumed that the particles, including a plurality of elements, are distributed throughout the filter surface, with the elements being present in the same proportions in each particles, according to the amounts present in the selected sample. That is to say, the elements drawn in by the multiple scans are assumed to be drawn up in the same proportion with each scan, and each monochometer is set to one wavelength to analyze one element during each scan. Elements of which the emission spectrum wavelenghts have been determined include, for example, Al, Fe, C, P, Si, Cu, B, K, Na, Ni, Cr, Ca, C1, F, N, W, Ti, Mo, Mg, Zn, Au, Co, Mn, Pb, 0, S, and Br.

Quality deterioration in semiconductor manufacturing, for example, is caused by inaccurate measurement of the elements, that is composition of an ingredient, and by inaccurate measurement of size or weight. Thus, by simply analyzing the average quantity of an element would not be sufficient to insure against quality deterioration.

SUMMARY OF THE INVENTION

The invention aims to resolve the foregoing and other problems and deficiencies of the prior art.

An object of the invention is to provide a particle component analyzing apparatus and method for measuring equivalent particle diameters and for determining particle compositions using such apparatus, wherein by obtaining equivalent particle diameters of individual particles and by identifying the compositions of the particles, extremely fine control is obtained, for example in the manufacture of semiconductors, and the like.

The foregoing object is attained by the invention which encompasses a particle component analyzing apparatus comprising an aspirator which scans a filter and draws particles collected thereon and wherein microwaves are used to excite the particles and cause them to emit an emission spectrum having a plurality of different wavelengths which is then guided to a plurality of monchrometers for measurement of the different wavelengths, and converted into electrical signals using optoelectrical converters, whereby the plurality of elements in the particles are identified. The particle component analyzing apparatus is provided with means for obtaining the cube roots of the outputs from the optoelectrical converters and by obtaining the ratio of cube root outputs corresponding to the diameters of the particles preprocessed into spherical form of a reference element and of an element to be measured, and then by obtaining the cube root of an output from an element in the measurement sample and by multiplying it by the ratio of cube root outputs with respect to the reference element, an equivalent particle diameter is obtained which is corrected for differences in sensitivity between the elements, and the composition of the particle is determined from the emission spectrum of the elements contained in the particle, and the composition ratios of the plurality of elements are calculated from the emission intensity.

BRIEF DESCRIPTION OF THE DRAWING

FIG. 24 is a graph depicting emission intensity ratios, with respect to C, of Si, N and S bonded to C, plotted on the vertical axis versus particle diameter of C, plotted on the horizontal axis, based on the results of FIG. 22.

FIG. 25 is a graph depicting changed emission intensity ratios, with respect to C of Si, N and S, versus the particle diameter of C, resulting from changes to the conditions of the manufacturing process by which the known powder of FIG. 22 was produced.

DETAILED DESCRIPTION OF THE PREFERRED EMBODIMENTS

Figure 1:
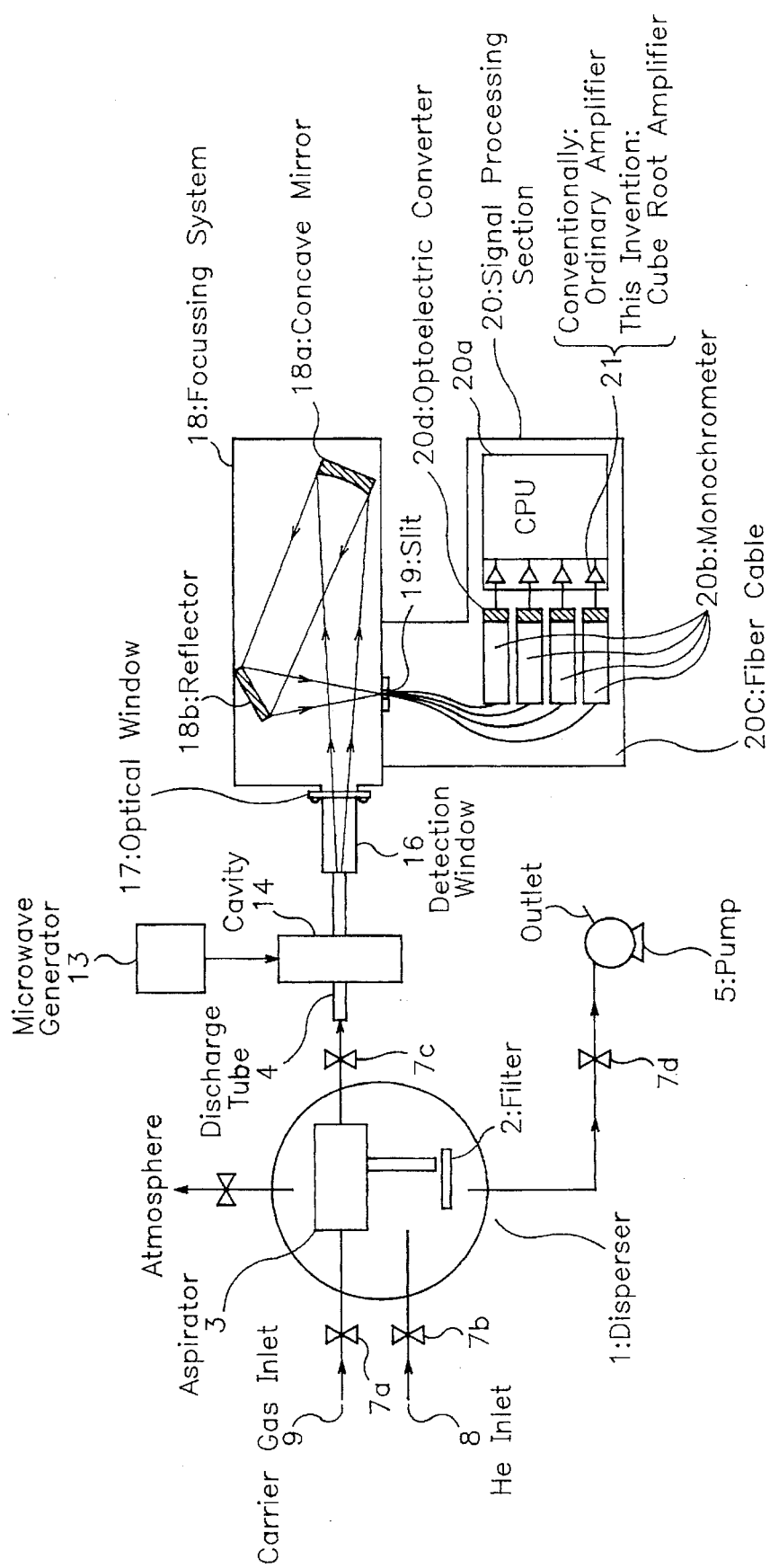
FIG. 1 is a diagram depicting a conventional apparatus. It is to be noted that when amplifier 21 is an ordinary amplifier, this apparatus is a conventional apparatus, and when amplifier 21 is a cube root amplifier, then the apparatus is an illustrative embodiment of the invention.
Figure 2:
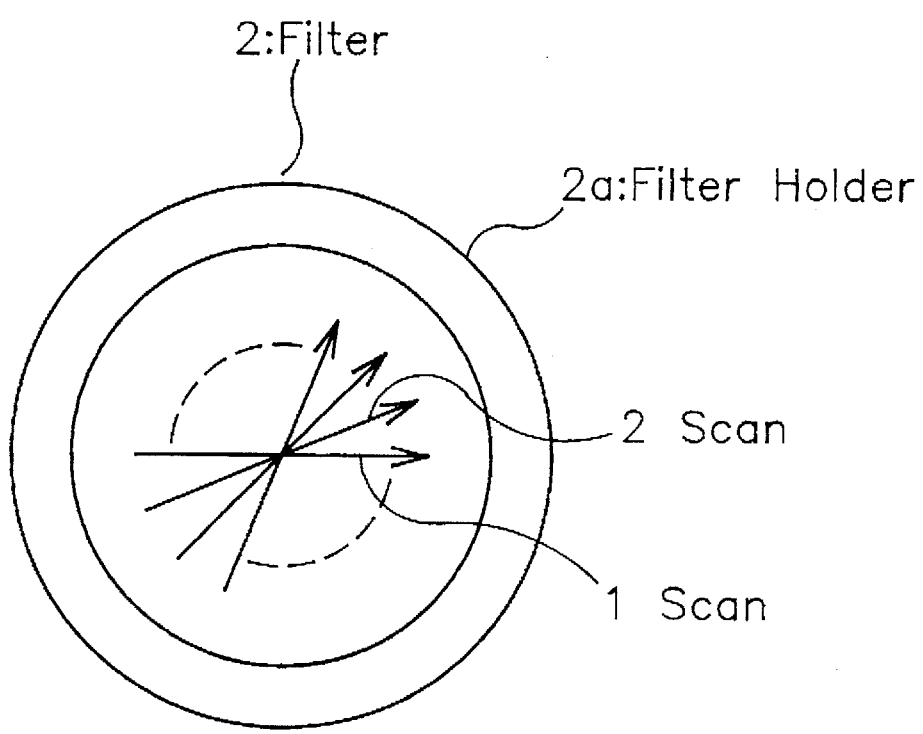
FIG. 2 is a view depicting how an aspirator scans a filter.

As above mentioned, FIG. 1 also shows an illustrative embodiment of the invention, when amplifier 21 is a cube root amplifier. The below discussion of the invention apparatus and method using same will thus refer to FIG. 1.

Figure 3:
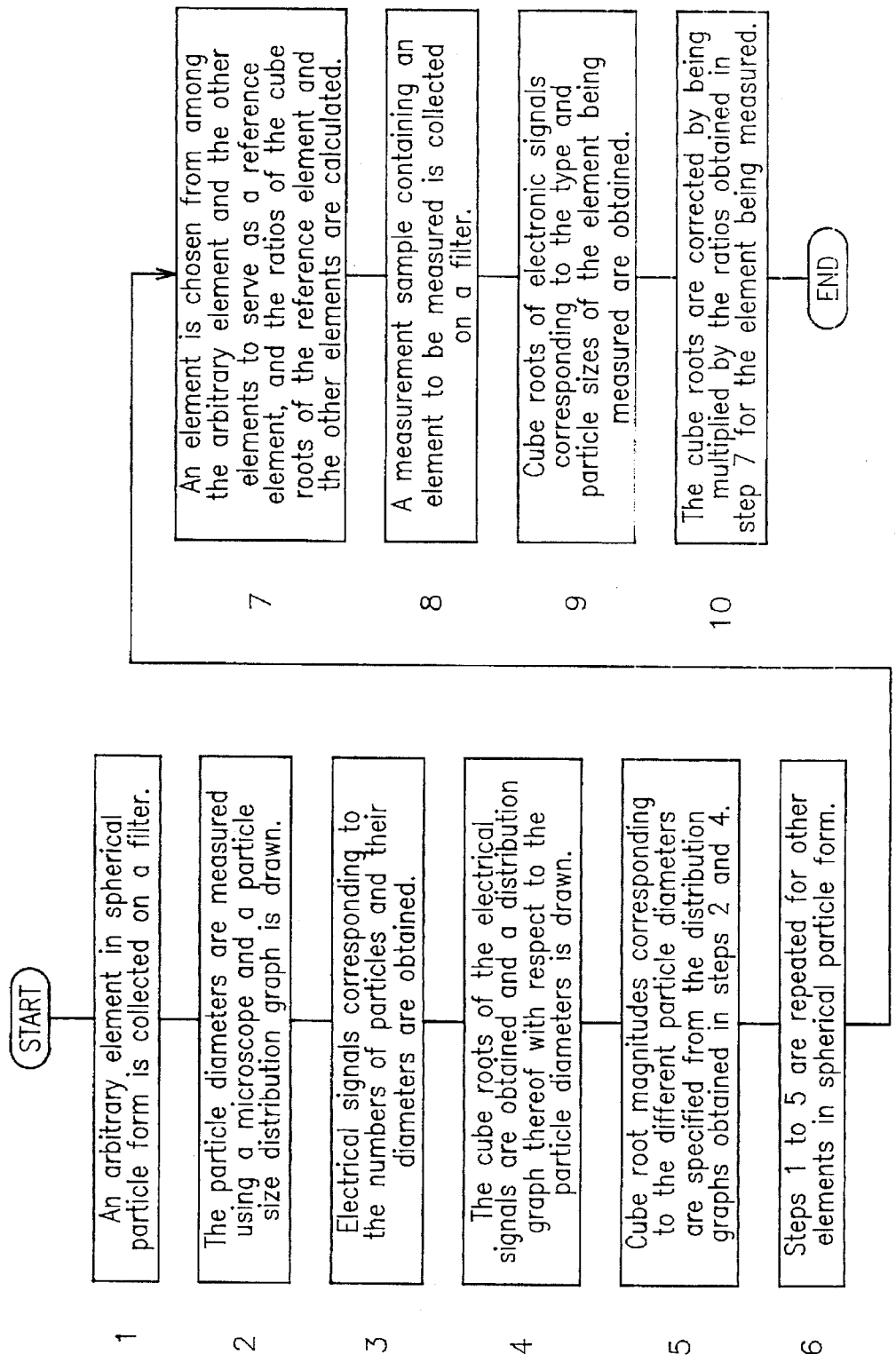
FIG. 3 is a flow chart depicting the procedure used in the analyzing method of the invention.

FIG. 3 shows the processing steps of the method of the invention, such as used inside the central processing unit 20a of FIG. 1. The values calculated in steps 1 to 7 of FIG. 3, are stored in the memory, for example, of the CPU, and analysis of measurement samples is carried out by performing steps 8 to 10. Also, in this preferred embodiment, light emitted by monochrometers 20b are converted into electrical signals by optoelectric converters and then processed in cube root amplifiers 21, A/D converted and inputted to the CPU. The embodiment involving four monochrometers will be described.

Figure 4:
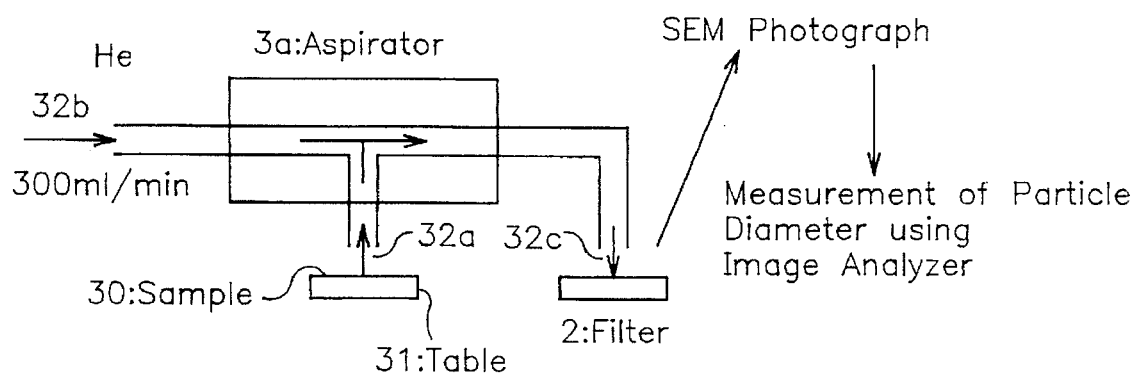
FIG. 4 is a view depicting an illustrative particle collecting apparatus of the invention.

In Step 1, spherical elements are collected on a filter. The collecting apparatus used for this function can, for example, be of the kind shown in FIG. 4. In FIG. 4, a standard sample 30, of Si of a nominal particle diameter of, for example 5 μm is scattered over a table 31. Standard samples of this kind are commercially available. An aspirator 3a, having a suction inlet 32a, is disposed above table 31. The standard sample is drawn in by suction inlet 32a being brought close to the surface of table 31 and a gas (e.g. nitrogen, air, helium, etc) being blown through the tube in the direction of arrow 32b to create reduced pressure at inlet 32a. A filter 2 is disposed at the outlet 32c of aspirator 3a, and the standard sample 30 is caused to travel to and to adhere to the surface of filter 2.

Figure 5:
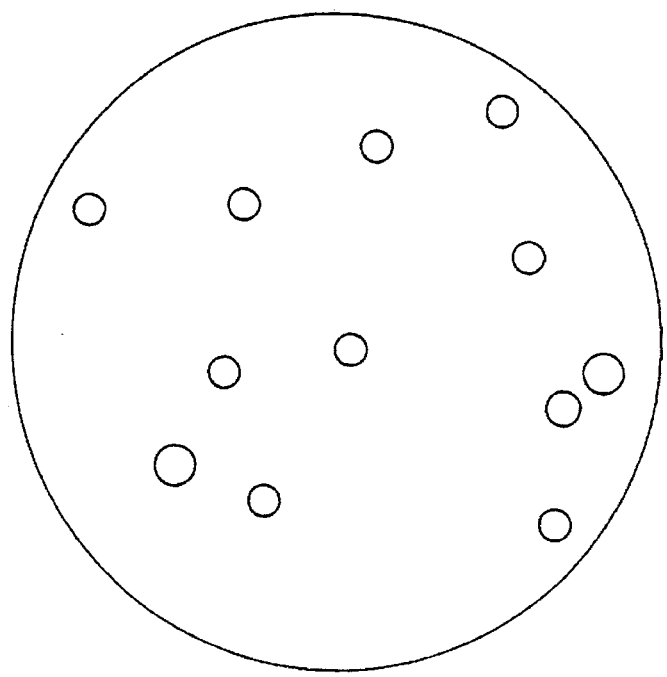
FIG. 5 is an SEM photograph depicting particles adhered to the surface of a filter.

FIG. 5 shows an SEM photograph of a number of Si particles adhered to the surface of filter 2. The individual particles are separated from each other because of shock waves generated as the gas is injected into aspirator 32. It can be seen from the photograph that although the particles are of nominal diameter of 5 μm there is some variation in their sizes.

Figure 6:
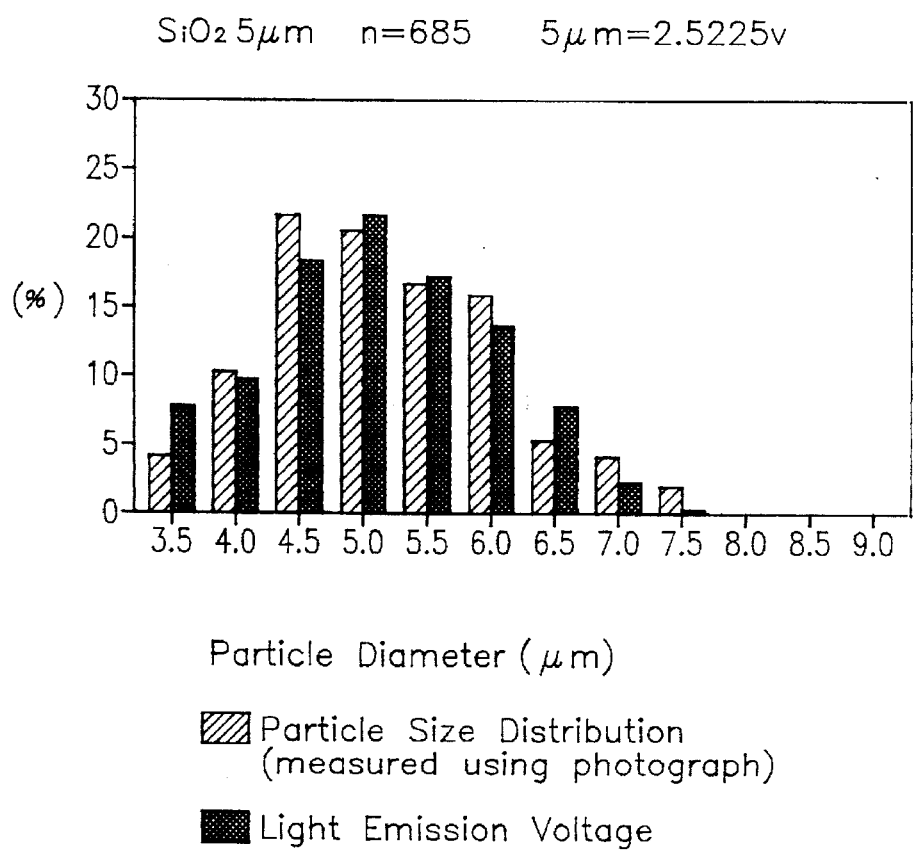
FIG. 6 is a graph depicting particle size distribution versus output of an analyzing apparatus.

In Step 2 of FIG. 3, an image analyzer (not shown in the drawings) is used to measure the particles using the SEM photograph. FIG. 6 shows the particle size distribution of $SiO_2$ by percentages using hatched bars. The solid bars will be explained later in connection with step four. Particles of diameter 4.5 μm were the most numerous, at about 22%, followed by those of diameter 5 μm, constituting about 21%. It can be seen that in $SiO_2$, sold as being of a diameter of 5 μm, there is a particle size variation of from 3.5 μm to 7.5 μm.

In step 3 of FIG. 3, filter 2 is loaded into the analyzing apparatus of FIG. 1, and in a plasma, the particles are atomized, and ionized and caused to emit an emission spectrum. This light is converted into electrical signals corresponding to the sizes of the particles and outputted by optoelectric converters 20d disposed in back of monochrometers 20b.

In this embodiment, aspirator 3 scans a predetermined area of filter 2 in a predetermined time, for example, 4 minutes, and a number of electrical signals, corresponding to the number of particles drawn in, are outputted.

In Step 4 of FIG. 3, the electrical signals obtained in Step 3 are inputted into cube root amplifiers 21 of FIG. 1, which output the cube roots of their inputs. The solid black bars of FIG. 6 show the percentage variations in the outputs of the cube root amplifiers 21. It can be seen that this variation substantially corresponds to the distribution of the particle sizes measured using the SEM photograph in Step 2.

In Step 5 of FIG. 3, outputs are specified for the particles based on the distribution chart of FIG. 6. In experiments carried out by the inventors, the output of a cube root amplifier 21 for a 5 μm particle was, for example, 2.5225 V. This value varies with the amplifier gain.

In Step 6 of FIG. 3, steps 1 to 5 are repeated for elements, such as, for example, Fe, Al, Cu, P in the form of particles of known size, for example, 5 μm, and the relationship between the particle sizes and the corresponding outputs are found for each element. Even when the particle sizes are the same, their emission intensities differ depending on the element.

In Step 7 of FIG. 3, taking the emission intensity of, for example, Si as a reference, the ratios of the emission intensities of the elements, obtained in Step 6, are calculated. These values are stored in the memory of the CPU 20a, and are used as correction coefficients.

In Step 8 of FIG. 3, a measurement sample containing the elements to be measured is prepared, for example, by drawing in air through a dust collector in a clean room for a predetermined time and adhering particles of collected dust to a filter.

In Step 9 of FIG. 3, a filter, with particles collected in Step 8 thereon, is loaded into the analyzing apparatus and outputs of the cube root amplifiers 21 proportional to the emission intensities of the elements, contained in the measurement sample, are obtained.

Because in the case of this apparatus there are used four monchrometers, by severally adjusting the set wavelengths of the monochrometers, measurement of four elements at a time is carried out.

In step 10 of FIG. 3, the cube root amplifier output, obtained for each element, are corrected by being multiplied by the respective correction coefficients stored in a memory in step 7, and the equivalent particle sizes of each element are calculated. Advantageously in the invention, the cube roots are obtained of the outputs of the optoelectric converters, so that the signals are compressed and their dynamic ranges are enlarged.

By the above process, the magnitudes of the volumes of the elements can be obtained from the equivalent particle diameters.

Figure 7:
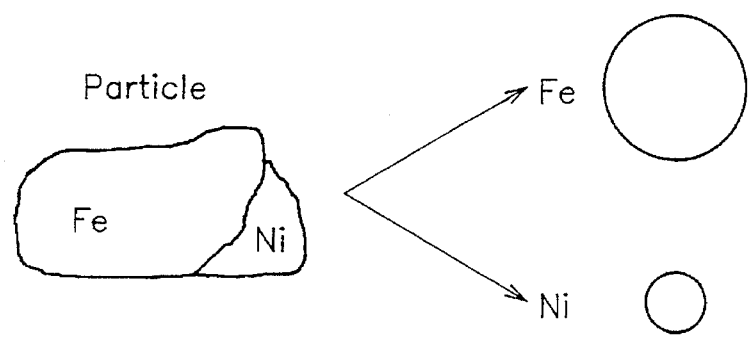
FIG. 7 is a view depicting a particle existing as a compound.
Figure 8:
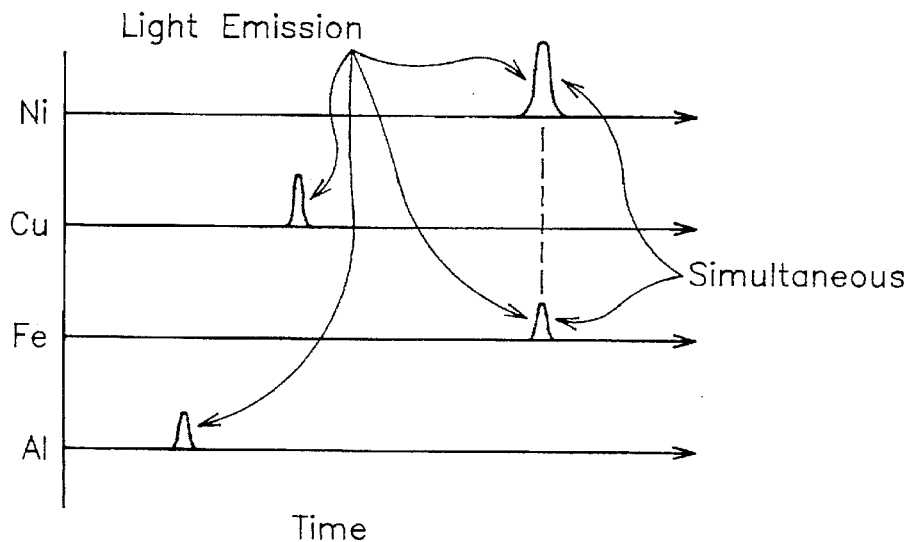
FIG. 8 is a view depicting two elements existing in one particle as manifested in the outputs of four monochrometers.

There may be cases when the elements exist in the measurement sample in the form of a compound. For example, if there is compound of Fe and Ni, such as shown in FIG. 7, assuming that the wavelengths for these two elements are among the set wavelengths of the four monochrometers 20b, because the outputs of the compound are simultaneous, there will be Ni and Fe emission spectrum at the same time, as shown in FIG. 8. In this case, also, because the amounts of emission spectrum, i.e. amounts of the outputs, differ according to the ratio of the elements in the compound, it is possible to obtain equivalent diameters corresponding to the ratio of the elements in the compound.

Although in the preferred embodiment, a case was discussed wherein the cube root amplifiers 21 are disposed as a stage after the optoelectric converters 20d, and carry out analog processing, it is also possible as means of obtaining cube roots to convert the signals from the optoelectric converters 20d into digital signals with an A/D converter and the carry out digital processing in a CPU. Any means, which obtains the cube roots of the outputs of the optoelectric converters 20d corresponding to the elements and sizes of the particles, will suffice, and the invention should be so construed as not being limited.

Figure 9:
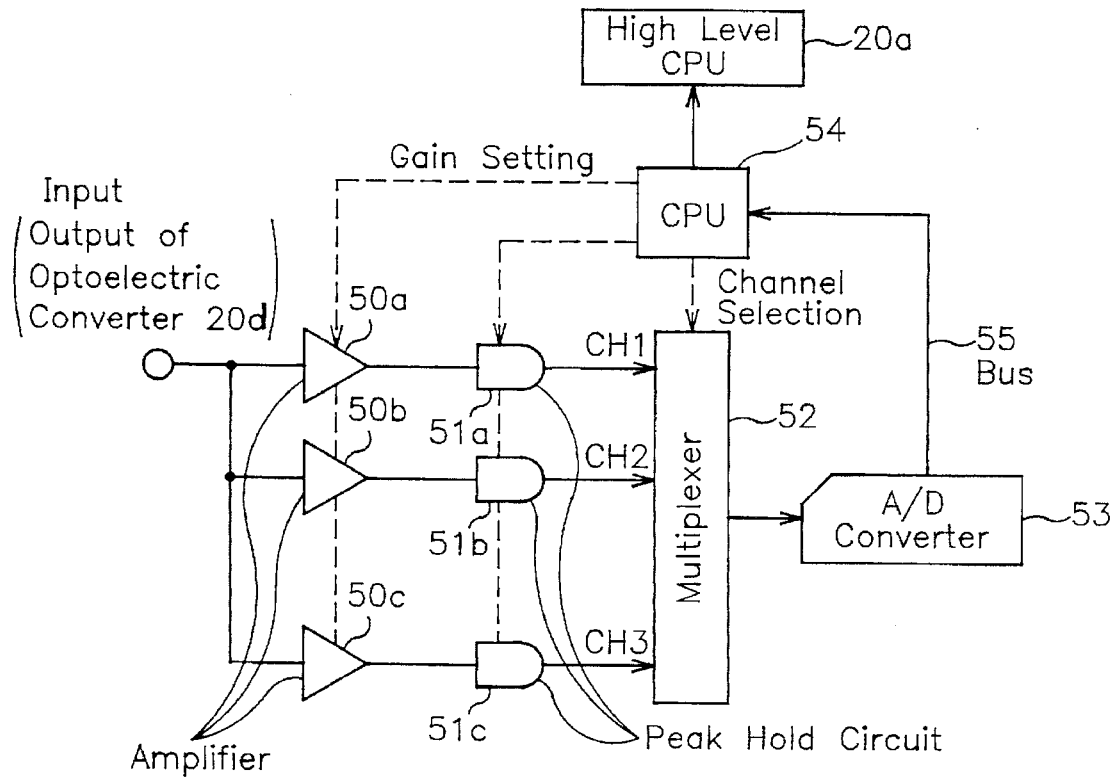
FIG. 9 is a diagram depicting circuitry for converting the signals of an optoelectric converter into digital signals using an Analog to Digital converter (A/D converter).

FIG. 9 shows the circuitry, provided for each optoelectric converter 21d, where output signals of converters 20d provided for each monochrometer 20b, are converted into digital signals by A/D converters 53. In FIG. 9, the output of each converter 20d is inputted into, for example, three amplifiers 50a,50b,50c.

Peak hold circuits 51a,51b,5cc are disposed in back of amplifiers 50a, 50b, 50c. A multiplexer 21 receives as inputs, the outputs of amplifiers 502,50b,50c, and hold circuits 51a,51b,51c. An A/D converter 53 converts the output of multiplexer 52 into digital signals, which are applied via bus 55 to CPU 54.

A CPU 54 sets the amplifier gains of amplifiers 50a,50b, 50c, resets peak hold circuits 51a,51b,51c, receives digital signals from A/D converter 53 through bus 55, and performs data processing according to the desired gain.

The output of CPU 54 is fed to a high level CPU 20a, where computation of cube roots determining diameters corresponding to the output signal of the optoelectric converters 20d is carried out.

Figure 10:
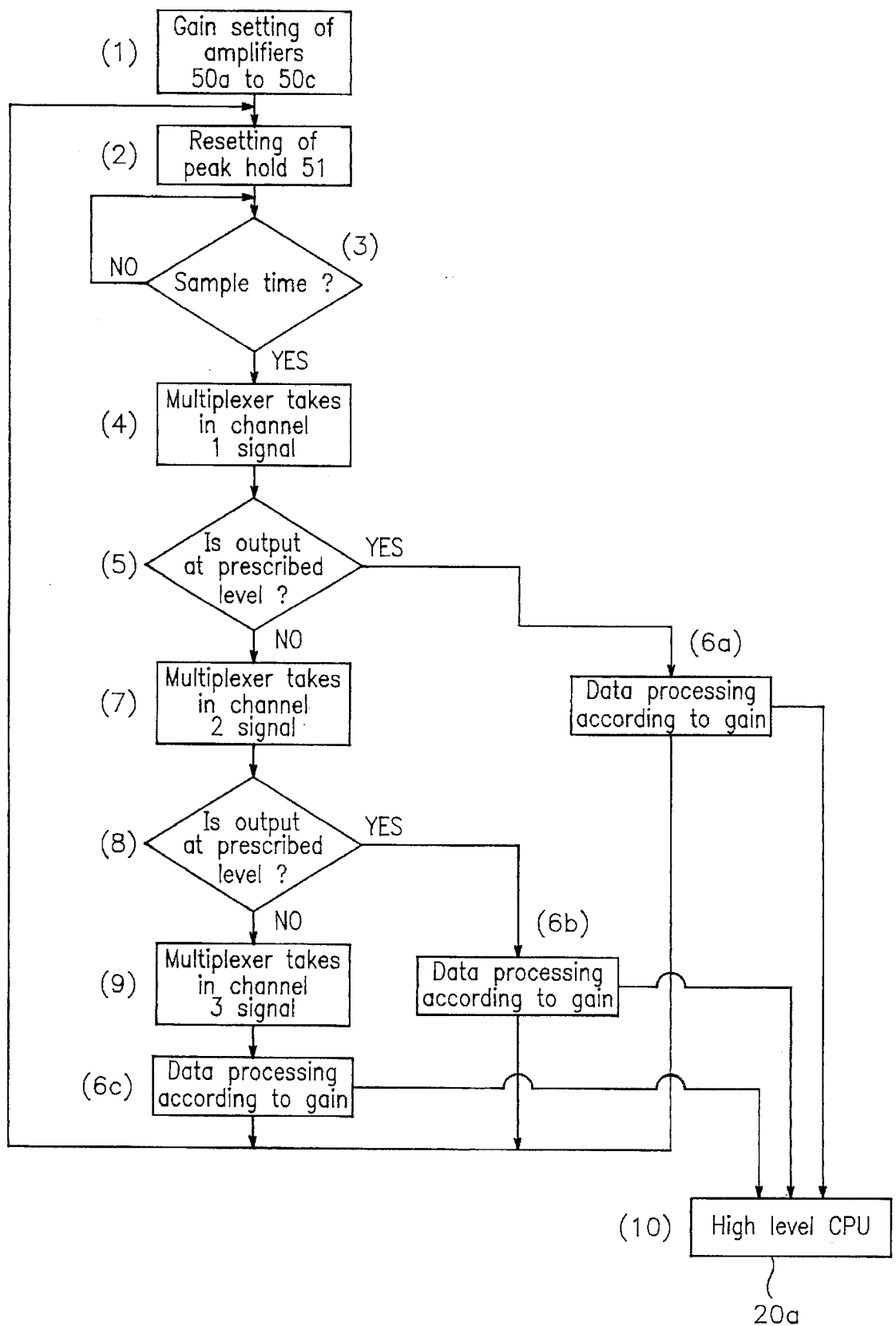
FIG. 10 is a flow chart depicting the process flow of the arrangement of FIG. 9.

FIG. 10 shows the process flow of the arrangement of FIG. 9. In Step 1, the gains of amplifiers 50a,50b, 50c are set to, for example, 0, 20 and 40 dB, by CPU 54.

In Step 2 of FIG. 10, CPU 54 resets the hold values of the peak hold circuits 51a, 51b, and 51c, and in Step 3, the CPU 54 judges whether or not it is sample time. If the answer is YES, in Step 4, a channel,e.g. 1, is selected to be inputted into multiplexer 52 according to a predetermined sequence. The resetting, sample time, and channel selection is performed according to a clock in CPU 54. In Step 3, if the answer is NO, the sample time is again determined, until a YES is obtained.

The signal inputted into multiplexer 52 is converted into a digital signal by A/D converter 53 and sent through bus 55 to CPU 54. In Step 5, CPU 54 judges whether or not the signal is above a predetermined level. If the judgement in Step 5 is YES, then in Step 6a, CPU 54 carries out data processing according to gain on the signal and transfers the signal to the high level CPU 20a in Step 10. If the judgement is NO in step 5, CPU does not perform data process of step 6a nor send the signal to CPU 20a; instead, in Step 7, the CPU 54 commands the multiplexer 52 to receive, in channel 2, the signal being held in peak hold circuit 51b.

The signal inputted into multiplexer 52 from peak hold circuit 51b, having been amplified 10 times (i.e. 20 dB) by amplifier 50b, is converted into a digital signal by A/D converter 53 and sent through bus 55 to CPU 54.

In Step 8, CPU judges whether or not the signal is above a predetermined level. If the judgement is YES, then in Step 6b, data processing is carried out according to gain on the signal and in Step 10 the signal is transferred to high level CPU 20a. If the judgement in Step 8 is NO, CPU 54 does not process the data in step 6b nor send the signal to the CPU 20a; rather, in Step 9, the CPU 54 commands multiplexer 52 to input in channel 3, the signal being held in peak hold circuit 51c.

The channel 3 signal inputted to multiplexer 52 from peak hold circuit 51c, having been amplified 100 times (i.e. 40 dB) by amplifier 50c, is converted into a digital signal by A/D converter 53, and transmitted through bus 55 to CPU 54. In Step 6c, the CPU 54 carries out data processing according to gain on the signal and transfers the signal in Step 10 to high level CPU 20a.

By the above process, it is possible, for example, to increase the output range from a range of 0 to 10 obtained when a single amplifier is used, to an expanded range of 0 to 1000. This increase in the dynamic range is especially beneficial when particle sizes are expressed by equivalent diameters.

In the preferred embodiment, the case in which there are three amplifiers, was discussed. However, two or four or more amplifiers may be used. Also, if CPU 54 is made to select channel 1 of the multiplexer first, peak hold circuit 51a disposed in back of amplifier 50a, can be dispensed with. Also, CPU 54 and CPU 20a, can be one central processing unit performing both functions.

In the preferred embodiment, the gains of amplifiers 50a, 50b, 50c, were set to 0, 20 and 40 dB, but the setup may be such that the gains are instead 40, 20 and 0 dB, and CPU 54 judge whether or not the output of amplifier 50a is saturated, and if it is saturated then select the hold value of amplifier 50b and judge whether or not that the latter is saturated, and again if amplifier 50b is saturated, the select the hold value of amplifier 50c.

Figure 11:
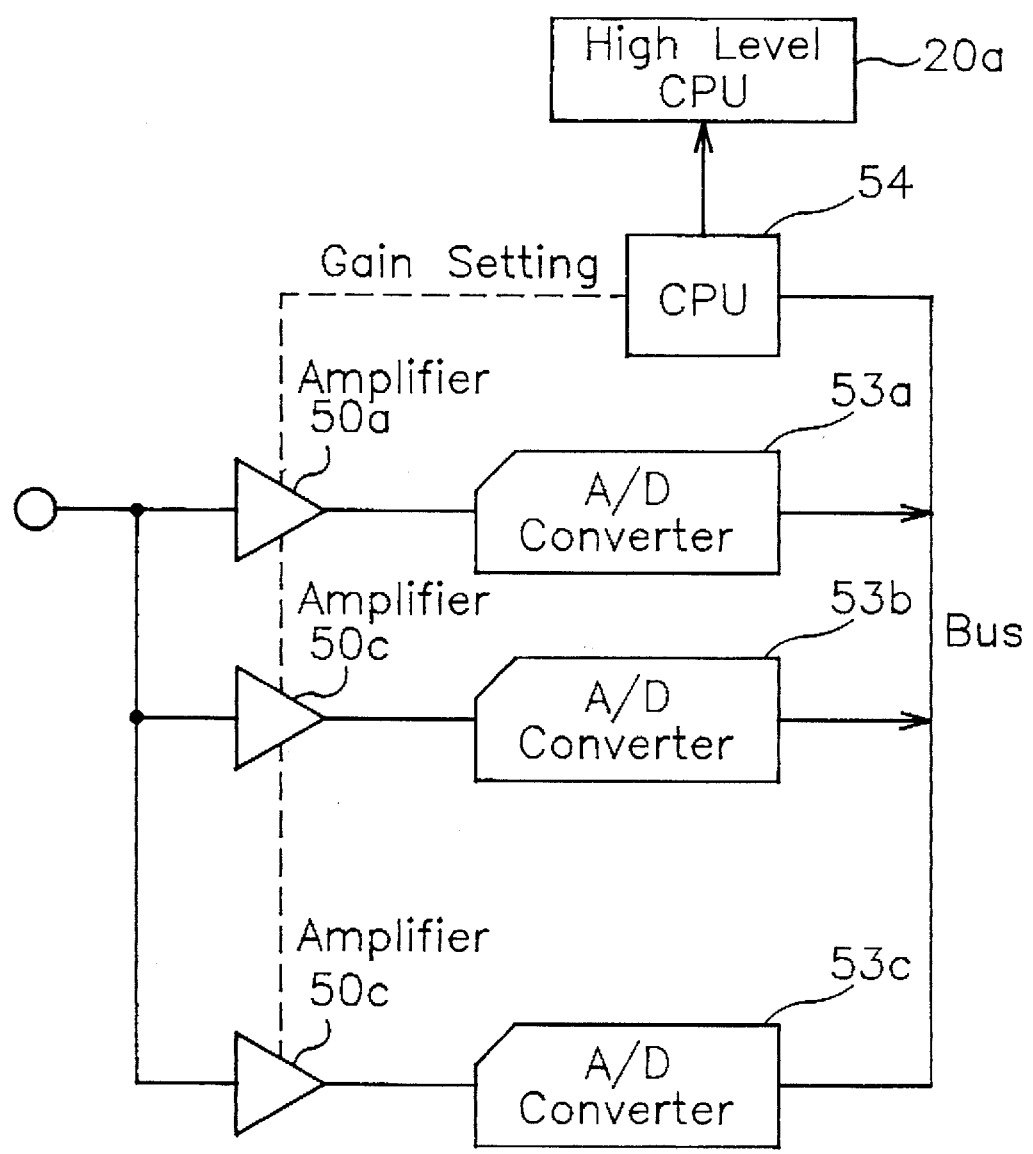
FIG. 11 is a view depicting an arrangement similar to FIG. 9.

FIG. 11 shows an arrangement wherein the outputs of amplifiers 50a, 50b, 50c are directly inputted into A/D converters 53a,53b, 53c, and CPU 54 sequentially directly reads out the outputs of A/D converters 53a, 53b, and 53c.

Figure 12:
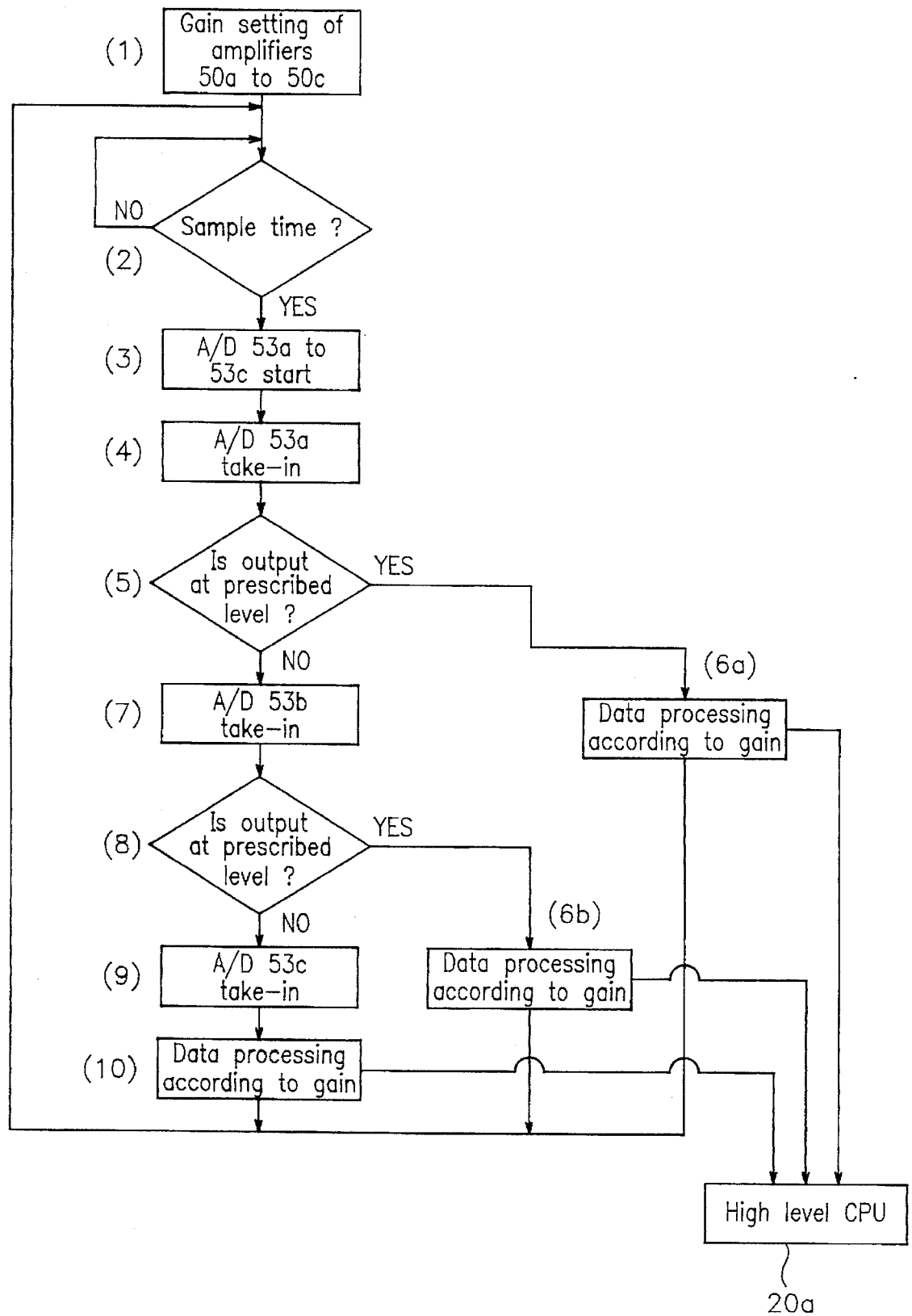
FIG. 12 is a flow chart depicting a process flow for the arrangement of FIG. 11.

FIG. 12 is a diagram illustrating the process flow of the arrangement of FIG. 11. In Step 1, the gains of amplifiers 50a, 50b, 50c are set to, for example, 0, 20 and 40 dB by CPU 54. Then, in Step 2, CPU 54 judges whether or not it is sample time. If the answer is YES, it goes to step 3, and according to a predetermined sequence, in step 4, the output of amplifier 50a is converted into a digital signal by A/D converter 53a, and sent through a bus 55 to CPU 54. If the answer is NO in Step 2, the sample time is again tested until the answer is YES. In Step 5, CPU 54 judges whether or not this signal is above a predetermined level. If the judgement is YES, then in step 6a, CPU 54 performs data processing according to gain on the signal, and transfers it to high level CPU 20a. If the judgement in Step 5 is NO, then CPU 54 does not process the data in Step 6a, nor send this signal to the high level CPU 20a; rather, in Step 7, CPU 54 inputs the signal from the A/D converter 53b, that has been amplified 10 times (i.e. 20 dB) by amplifier 50b.

Then, in Step 8, CPU 54 judges whether or not that signal is above a predetermined level. If the judgement is YES, then in Step 6b, CPU 54 performs data processing on the signal according to gain, and transfers the signal to high level CPU 20a. In Step 8, if the judgement is NO, then CPU 54 does not perform data processing in Step 6b, nor send the signal to high level CPU 20a; rather, CPU in step 9 inputs the signal from A/D converter 53c that has been amplified 100 times (i.e. 40 dB) by amplifier 50b, and in step 10 performs data processing on the signal according to gain and transfers the signal to high level CPU 20a.

With the above arrangement, and flow process, compared to the arrangement and flow process of FIGS. 9 and 10, because the signals do not pass through a multiplexer, the processing speed is correspondingly increased.

In the apparatus described, four monochrometers and four cube root amplifiers were used to simultaneously measure four different elements. However, because these devices have individual differences a difference in output occurs even when these devices measure elements of the same diameter at the same time. To resolve this problem, in the invention, the output of an arbitrary monochrometer is, for example made to be 1. With this as a reference, the outputs of the other monchrometers are standardized, for example to 0.9 and 1.1, etc. and the outputs of the monochrometers are corrected, based on those standardized values. In this way, it is possible to make the corrections to the outputs of the monchrometers.

Next, a method of determining the composition of a particle from synchronized detected elements contained therein, and a method for computing the composition ratios of a plurality of elements from their emission intensities, will be described.

Figure 13:
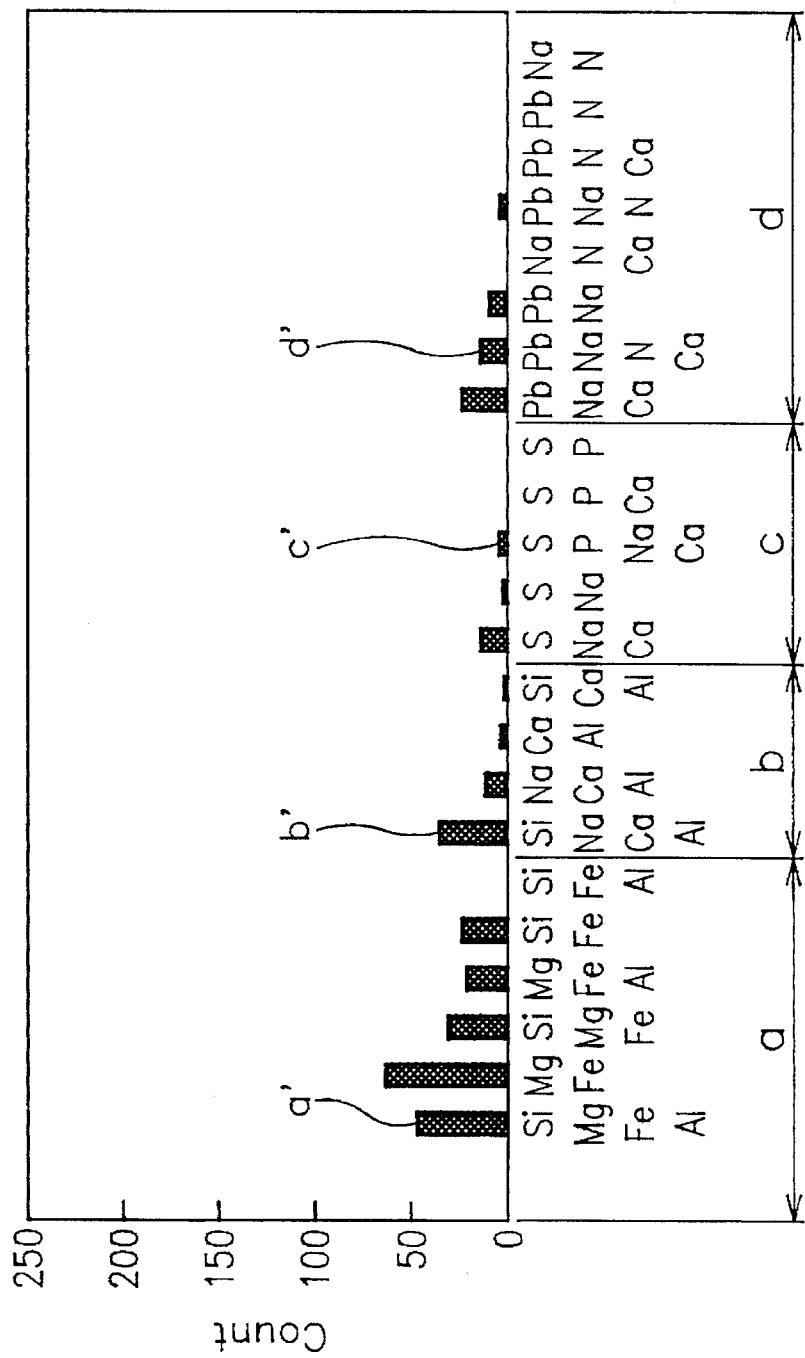
FIG. 13 is a chart depicting the results obtained when the monochrometers were set to wavelengths of different elements for four scans, and the numbers counted of the synchronized detected elements.

FIG. 13 shows the results obtained when airborne particles were deposited on the surface of the filter of the apparatus described above, using a cyclone dust collector or the like, and the set wavelengths of the 4 monochrometers were set to the wavelengths of different elements each time the aspirator scanned the filter; and the number of synchronized detected elements was counted. The vertical axis shows the number of synchronized detected elements counted. The horizontal axis shows what the synchronized detected elements were. The intervals labeled a to d are four different scans in which the monochrometers were set to the wavelengths of the four groups of elements a' to d', respectively.

That is to say, in the scan in range a, the monchrometers were set to the wavelengths of elements Si, Mg, Fe and Al, and these elements were synchronized detected approximately 50 times. Mg and Fe were synchronized detected about 65 times. Synchronized detected elements of other combinations are also shown. It can be seen that in the range a, the number of tiem Si, Fe and Al was synchronized detected was too small to be shown in the graph.

In scanning range b, the monochrometers were set to the wavelenghts of the elements Si, Na, Ca and Al, and in scanning range C the monchrometers were set to the wavelengths of elements S,P,Na and Ca.

Looking more closely at the results of the scanning during interval a, it can be seen that simultaneous emission spectrums of Si and Mg, and Si and Fe, were the most numerous.

Figure 14:
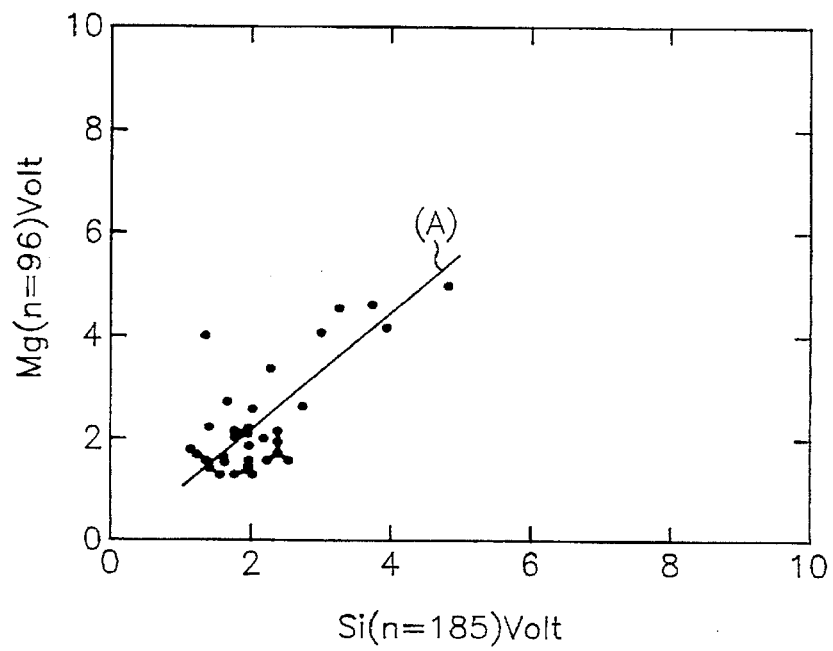
FIG. 14 is a graph depicting the relationship between the emission intensity of Mg and the emission intensity of Si, based on the results of a scan in the range a of FIG. 13.
Figure 15:
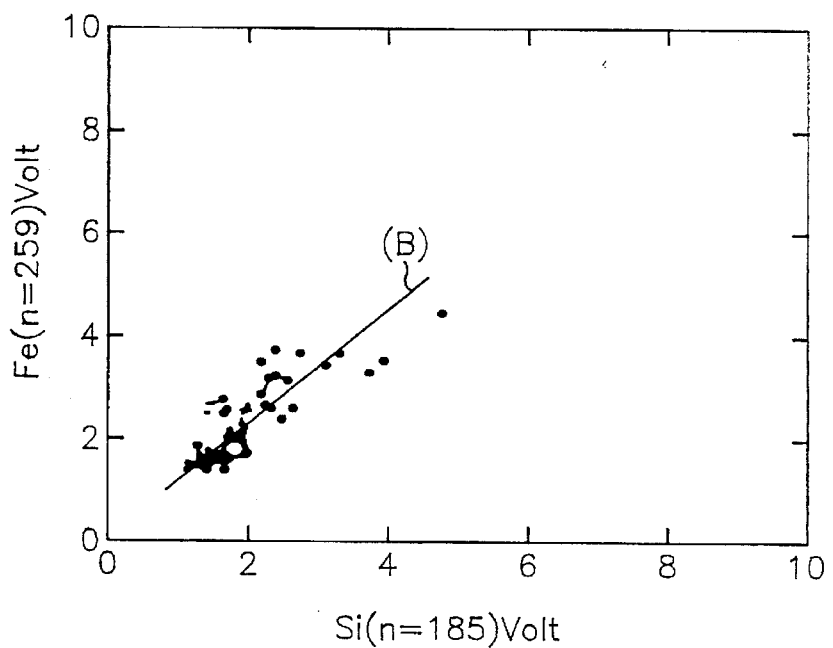
FIG. 15 is a graph depicting the relationship between the emission intensity of Fe and the emission intensity of Si, based on the results of a scan in the range a of FIG. 13.
Figure 16:
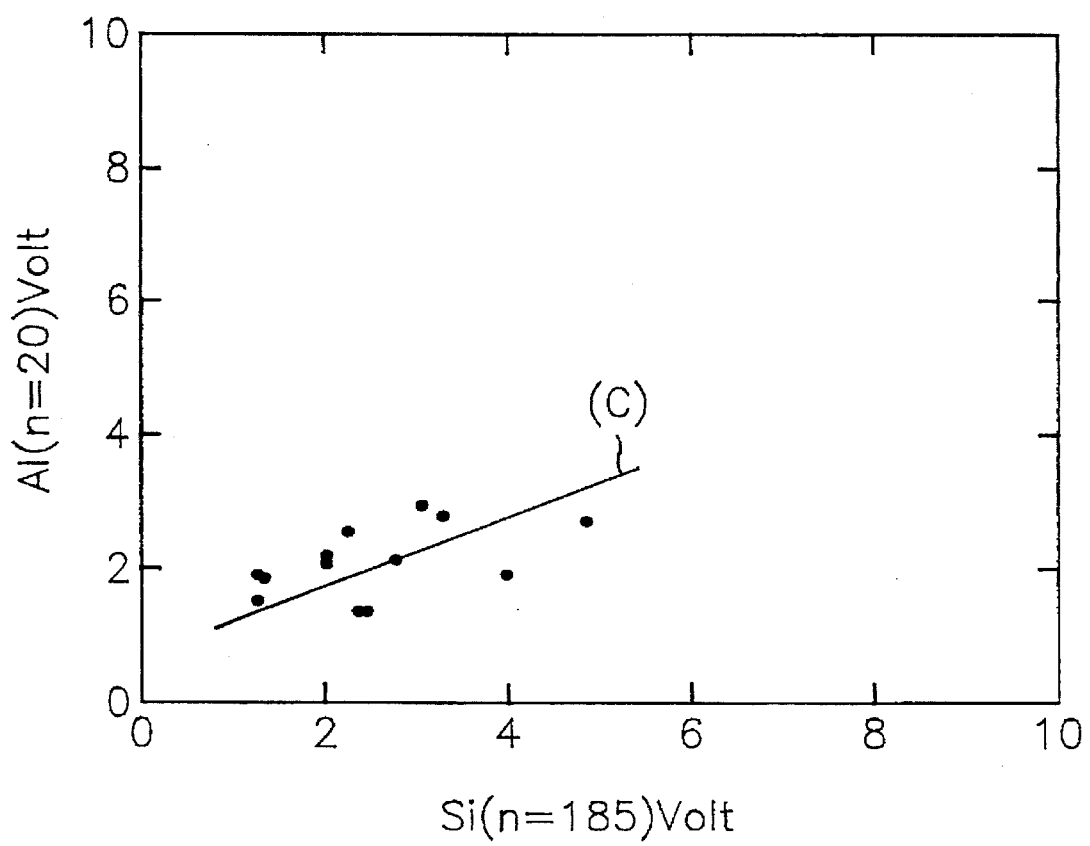
FIG. 16 is a graph depicting the relationship between the emission intensity of Al and the emission intensity of Si, based on the results of a scan in the range a of FIG. 13.

FIGS. 14, 15 and 16 show the relationships between the emission intensities, as measured in volts, of Mg, Fe and Al and those of Si, based on the measured results in range a shown in FIG. 13. FIG. 14 shows the relationship between Si and Mg. FIG. 15 shows the relationship between Si and Fe. FIG. 16 shows the relationship between Si and Al. In these graphs n is the number of emission spectrums in the scan. As can be seen from the graphs, there are fixed correlations between the emission intensity of the elements, shown by straight lines A,B and C. That is to say, although the emission intensity varies with particle size, if the emission intensity of one of the elements increases, that of the other element also increases. This indicates that irrespective of the size of the particle, Si, Mg and Fe are present in fixed ratios. Thus, it can be inferred that the particles exist as compounds and the gradients of the straight lines A, B and C show the composition ratios of the compounds. Using this index, it is possible to obtain detailed information on the compositions of the particles of matter.

Figure 17:
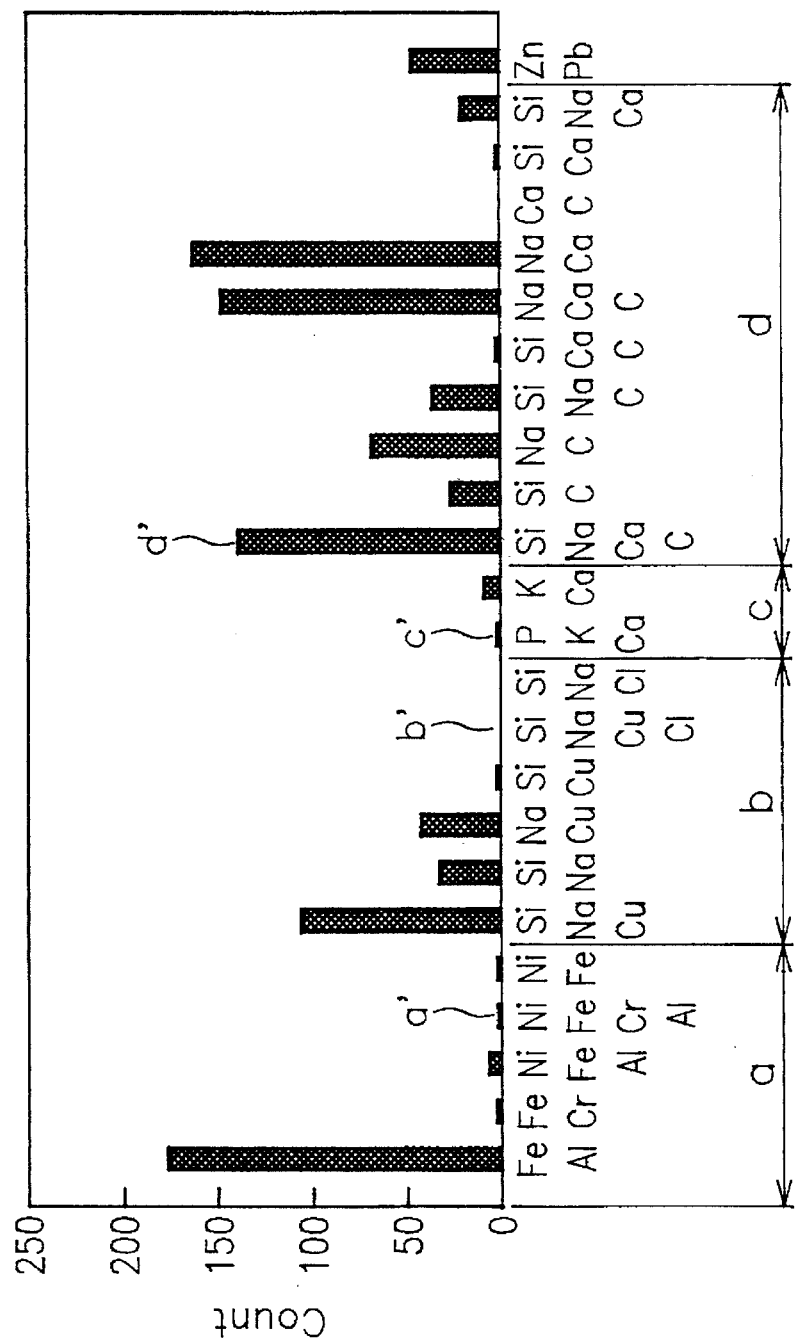
FIG. 17 is a chart depicting the results obtained when the monochrometers were set to the wavelengths of different elements for each scan and synchronized detected elements were counted.

FIG. 17 is a chart showing the results obtained when particles were similarly collected on a filter in a different atmosphere to that in the case discussed above, and when the 4 monochrometers were set to different wavelength each time the aspirator scanned the filter, and when the number of synchronized detected elements (see horizontal axis) was counted (see vertical axis). Intervals a to d are four different scans in which the monchrometers were set to the wavelengths of four groups of elements (a' to d') respectively. That is, in the scan of the range indicated by a, the monochrometers were set to the wavelengths of elements Ni, Fe, Cr and Al, and all of these elements were synchronized detected a small number of times. Fe and Al were synchronized detected about 180 times. Also, there were a small number of synchronized detected elements in other combinations.

In the range of scanning indicated by interval b, the monochometers were set to wavelengths of elements Si, Na, Cu and $_c$1. It can be seen that the number of times all of these elements were synchronized detected was too small to be shown on the chart, and that Si, Na and Cu were synchronized detected about 110 times. In the scan in the range of d, the monochrometers were set to the wavelenghts of Si, Na, Ca and C. All of these elements were synchronized detected about 140 times. Na, Ca and C were synchronized detected about 150 times. Na and Ca were synchronized detected about 170 times.

Figure 18:
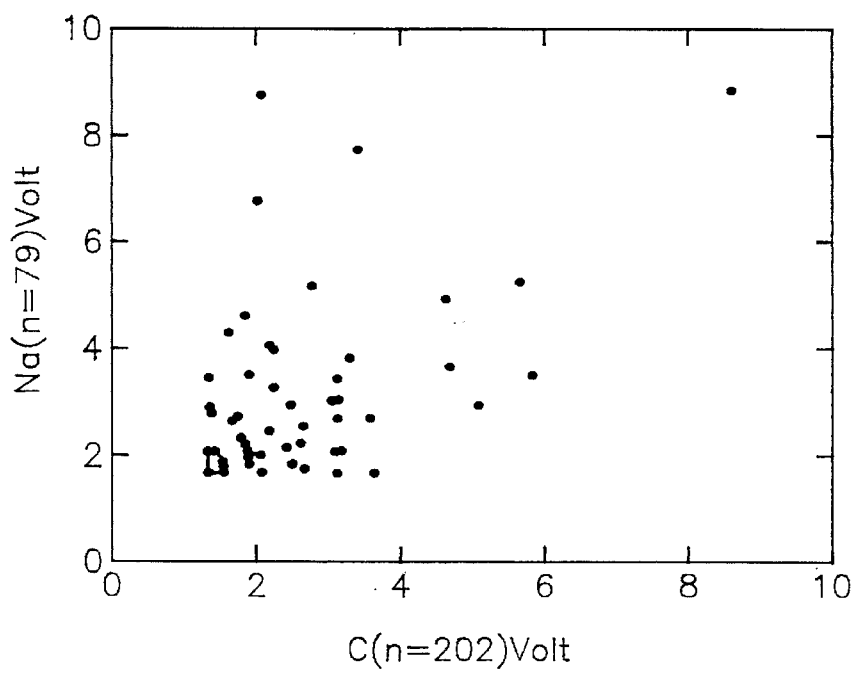
FIG. 18 is a graph depicting the relationship between the emission intensity of Na and the emission intensity of C, based on the results of a scan in the range d of FIG. 17.
Figure 19:
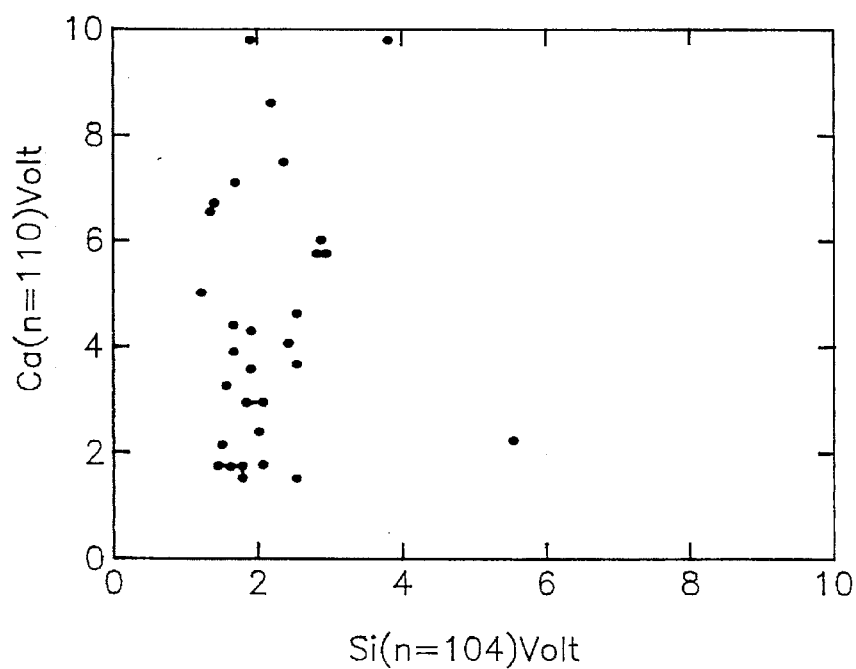
FIG. 19 is a graph depicting the relationship between the emission intensity of Ca and the emission intensity of Si, based on the results of a scan in the range d of FIG. 17.
Figure 20:
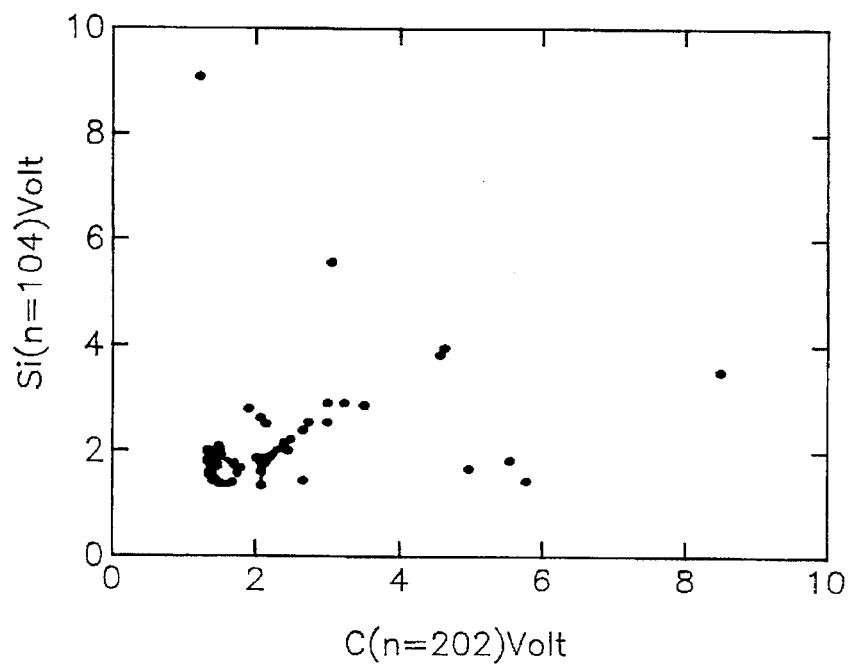
FIG. 20 is a graph depicting the relationship between the emission intensity of Si and the emission intensity of C, based on the results of a scan in the ranged of FIG. 17.
Figure 21:
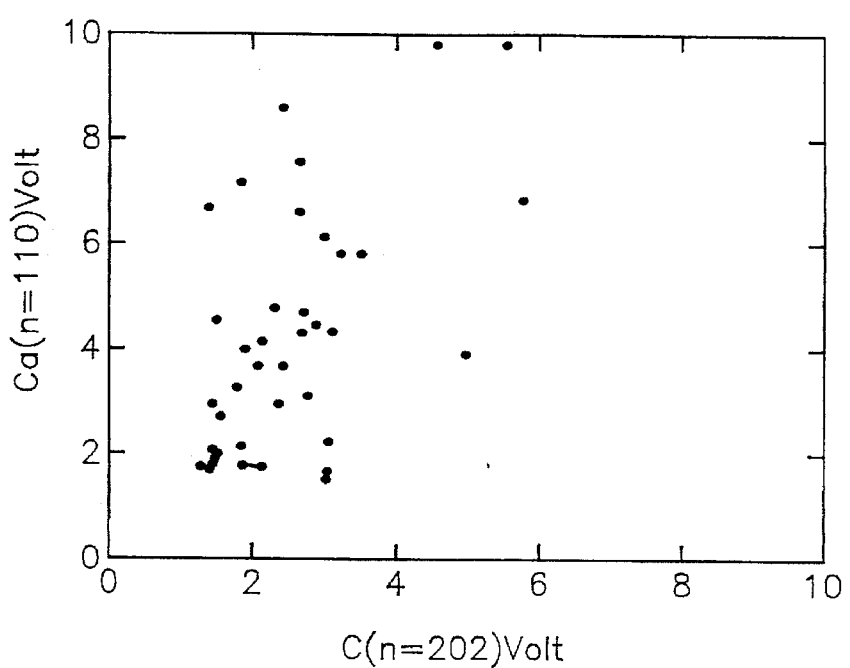
FIG. 21 is a graph depicting the relationship between the emission intensity of Ca and the emission intensity of C, based on the results of a scan in the ranged of FIG. 17.

FIGS. 18 to 21 are graphs wherein are plotted the relationship between the emission intensity (shown by volts) of elements C and Na (FIG. 18); Si and Ca (FIG. 19); C and Si (FIG. 20); and C and Ca (FIG. 21) in the range of d. It is not possible in any of the graphs to draw a straight line, like straight lines A,B, C shown in FIGS. 14 to 16. That is to say, the emission intensity varies with particle size, but there is no correlation between when the emission intensity of one of the elements increases and when the other element emission intensity increases. This means that these elements are present only as lumps and not as compounds.

Figure 22:
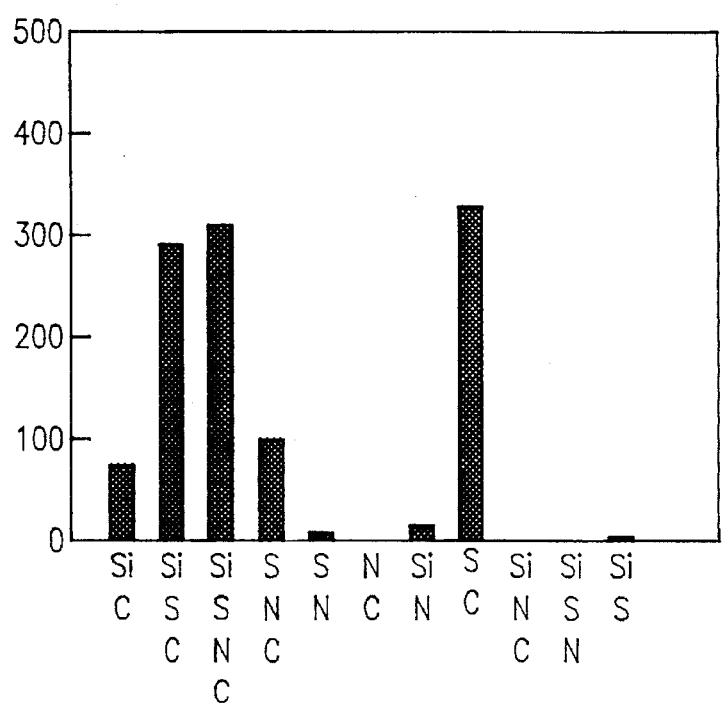
FIG. 22 is a chart depicting the results obtained when, with a powder of known composition, the monochrometers were set to the wavelengths of different elements and synchronized detected elements were counted.
Figure 23:
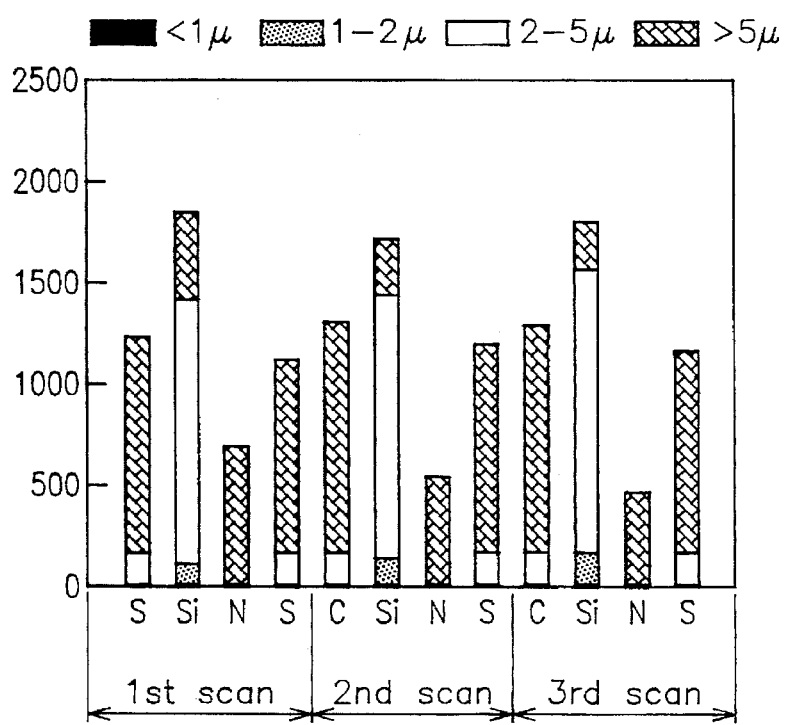
FIG. 23 is a chart depicting the relationship between the number of synchronized detected elements and the sizes of the elements for each of the three scans of the known powder of FIG. 22.

FIGS. 22 and 23 show results obtained when a functional material consisting of a mixed powder of a known composition (C, Si, N, S) was analyzed with the above described apparatus. FIG. 22 shows the number of synchronized detected elements (see vertical axis) and the elements (see horizontal axis), in one scan. FIG. 23 shows the number of synchronized detected (see vertical axis) of each element (see horizontal axis) per scan, and the sizes of the elements expressed in particle diameters. Three scans were carried out. In all three scans, the element count and the sizes were approximately the same, thus showing that the elements were evenly distributed over the filter surface.

FIGS. 24 and 25 show the densities (i.e. proportion, by voltage ratio) of Si and N and S with respect to the particle diameter of C (1.e. voltage). The functional materials shown in FIGS. 24 and 25 were produced by different manufacturing processes. By making clear these relationships between particle diameter and component density and functional material quality, it is possible to carry out quality control in an effective and reliable manner. FIGS. 13 to 25 show results computed by a CPU corresponding to CPU 20a of FIG. 1, as displayed on an CRT.

Advantageously, with the invention, in analyzing solid particles, by obtaining equivalent particle diameters of constituent elements and by determining what kind of compound (i.e. compositions) particles exist, as, for example, semiconductor manufacturing and the like, extremely fine control is made possible, and fine particle component analysis of increased dynamic range is made possible.

The foregoing description is illustrative of the principles of the invention. Numerous extensions and modifications thereof would be apparent to the worker skilled in the art. All such extensions and modifications are to be considered to be within the spirit and scope of the invention.

What is claimed is:

1. A method of determining the composition and characteristics of particles comprising a plurality of elements, said method comprising the steps of:

(1) setting a plurality of monochrometers to detect a plurality of different wavelenghts of said plurality of elements;

(2) scanning a filter to draw particles collected thereon;

(3) applying microwave induced plasma to said particles to cause said particles to emit an emission spectrum having a plurality of different wavelenghts indicative of said plurality of elements comprising said particles;

(4) synchronously detecting the plurality of wavelenghts in the emission spectrum of said plurality of elements using said plurality of monochrometer;

(5) counting the number of particulars ones of the synchronously detected plurality of elements in each emission spectrum;

(6) determining a correlated relationship of emission intensity of one element of the synchronously detected plurality of elements in each emission spectrum against emission intensity of one or more other elements of the synchronously detected plurality of element in each emission spectrum; and (7) determining existence of said plurality of elements as a compound or mixture, and ratio of elements using said correlated relationship obtained in the prior step.

2. The method of claim 1, wherein the particles being collected are in a controlled atmosphere.

3. The method of claim 1, wherein existence of said plurality of elements as a mixture is determined by the existence of indeterminate correlation between the relationship of emission intensity of one element of the synchronously detected plurality of elements in each emission spectrum against emission intensity of one or more other elements of the synchronously detected plurality of elements in each emission spectrum.

4. The method of claim 1, wherein step (1) through (7) are repeated a plurality of times, and substantially the same results are obtained to thereby indicate a substantially even distribution of mixed powder of said plurality of elements over said filter.

5. The method of claim 1, wherein the relationship of emission intensities are calculated with respect to particular diameters of said particles.

6. A method of determining the composition and characteristics of particles comprising a plurality of elements, said method comprising the steps of:

(1) setting a plurality of monochrometers to detect a plurality of different wavelengths of said plurality of elements;

(2) scanning a filter to draw particles collected thereon;

(3) applying microwave induced plasma to said particles to cause said particles to emit an emission spectrum having a plurality of different wavelengths and emission intensities indicative of said plurality of elements comprising said particles;

(4) detecting the plurality of different wavelengths and emission intensities in the emission spectrum of said plurality of elements using said plurality of monochrometers;

(5) synchronously detecting elements and counting the number of particular ones of the synchronously detected elements;

(6) determining a relationship between the emission intensities of one of the synchronously detected elements and another one or more of the synchronously detected elements; and (7) determining existence of said plurality of elements as a compound or mixture, and ratio of elements using said relationship obtained in the prior step.

7. The method of claim 6, wherein said particles being collected are in a controlled atmosphere.

8. The method of claim 6, wherein existence of said plurality of elements as a mixture is determined by existence of an indeterminate relationship between the emission intensities of one of the synchronously detected elements and another one or more of the synchronously detected elements.

9. The method of claim 6, wherein steps (1) through (7) are repeated a plurality of times and substantially the same results are obtained.

10. The method of claim 6, wherein said relationship between the emission intensities is calculated with respect to particular diameters of said particles.

* * * * *